United States Patent [19]
Watanabe

[11] Patent Number: 5,230,620
[45] Date of Patent: Jul. 27, 1993

[54] ORTHODONTIC BUCCAL TUBE

[76] Inventor: Kazuya Watanabe, Ushio Heights 205, 7-14, Shinden 2-chome, Ichikawa-shi, Chiba-ken, Japan

[21] Appl. No.: 809,963
[22] Filed: Dec. 18, 1991
[51] Int. Cl.$^5$ ................................................ A61C 3/00
[52] U.S. Cl. .................................................... 433/17
[58] Field of Search ............................. 433/8, 9, 17

[56] References Cited

U.S. PATENT DOCUMENTS

| | | | |
|---|---|---|---|
| 3,460,254 | 8/1969 | Scheuer | 433/8 |
| 4,196,517 | 4/1980 | Forster | 433/17 |
| 4,268,249 | 5/1981 | Forster | 433/10 |
| 4,498,867 | 2/1985 | Kesling | 433/17 X |
| 4,655,708 | 4/1987 | Fujita | 433/17 X |
| 4,963,092 | 10/1990 | Snead | 433/17 |

FOREIGN PATENT DOCUMENTS 3318725 11/1984 Fed. Rep. of Germany .......... 433/9

OTHER PUBLICATIONS

American Orthodontic Catalog, May 17, 1979, pp. 2-4.

*Primary Examiner*—Gene Mancene
*Assistant Examiner*—Nicholas D. Lucchesi
*Attorney, Agent, or Firm*—Flynn, Thiel, Boutell & Tanis

[57] ABSTRACT

An orthodontic buccal tube has an effective height of the main body of the tube restricted to a certain value by removing a portion corresponding to tie wings at the same time there are provided a groove for receiving a ligature in a part on the occlusal side, proximal to a tooth, of the main body of the tube and a recess portion capable of receiving the extremity of an instrument for dental surgery such as a pincette, etc. at a required position on the frontal surface of the main body of the tube, in order to solve problems of prior art orthodontic buccal tubes.

4 Claims, 2 Drawing Sheets

ORTHODONTIC BUCCAL TUBE

FIELD OF THE INVENTION

The present invention relates to an improvement of an orthodontic buccal tube.

BACKGROUND OF THE INVENTION

Heretofore a buccal tube as indicated in FIG. 4 was often used as an orthodontic buccal tube.

In the same figure, reference numeral 1 is a base portion of the buccal tube and 2 is the main body of the tube. In the main body 2 of the tube there are formed throughholes 3 and 4 having rectangular cross-sections, which traverse it in the longitudinal direction. The occlusal throughhole 3 is called the "main tube" and the gingival throughhole 4 is called the "auxiliary tube". A cover cap 5 is easily dismountably connected to the throughhole 3 serving as the main tube. Further, two tie wings 6 are formed on the occlusal side of the main body 2 of the tube, protruding therefrom in one body, and a hook 7 is added thereto on the gingival side.

FIG. 5 shows a state, in which the buccal tube described above is mounted on a first molar tooth of the lower jaw. In this case, the buccal tube is secured previously by welding at the base portion 1 to a band 9 fitted to the first molar tooth. The buccal tube or a bracket is secured directly by adhesion using an adhesive to other molar teeth. 10 indicates a rectangular wire for orthodontic treatment.

In the case where orthodontia is effected by using the buccal tube described above, the buccal tube is bonded on a tooth or welded on a band which is fitted to a tooth and the wire 10 is inserted in the throughhole 3 serving as the main tube.

In a buccal tube with torque the throughhole 3 described above having a rectangular cross-section is disposed with a certain inclination with respect to the tube base 1 and the buccal tube is so designed that an orthodontic force is produced by a torque generated after inserting the wire therein. The gingival throughhole 4 is used for an auxiliary wire pass.

The tie wings 6 above formed on the occlusal side of the main body 2 of the tube in one body, protruding therefrom, are used for passing a ligature 11 (or elastic module) between the gingival side portion of the main body 2 of the tube and, and the tie wings as indicated in FIG. 6, after having removed the cover cap 5 on the throughhole 3 serving as the main tube in order to prevent the wire from slipping out, i.e. as a portion for hooking the ligature.

The positional relation of the molar tooth of a patient, for which orthodontic treatment is required, is not, in most cases, in a good state. For this reason, even if the position of the buccal tube on the band is set so as to be most suitable, it happens often that the cusp of the opposite tooth is brought into contact with the tie wings described above so that the buccal tube cannot be set at a desired position, or even if it is set, the tie wings need to be removed thereafter by cutting by means of a cutting machine such as a dental engine, with a carborundum point.

Furthermore, in the case where the buccal tube is secured directly to the surface of a tooth by adhesion without a band, since the tube is constructed so that it cannot be easily held by means of a dental pincette, etc., it is also a disadvantage thereof that holding it, until the adhesive is hardened, is difficult.

OBJECT OF THE INVENTION

The present invention has been done in order to remove the disadvantages of the prior art buccal tube constructed as described above, and a principal object thereof is to provide an orthodontic buccal tube, by which ligation by means of a ligature is possible, although there are no tie wings, and which can be firmly held while securing it to a tooth by adhesion using an adhesive.

SUMMARY OF THE INVENTION

In order to achieve the above object, in an orthodontic buccal tube according to the present invention, the effective height of the main body of the tube is restricted to a certain value by removing a portion corresponding to the tie wings; at the same time there is disposed a groove for receiving a ligature at a part on the occlusal side, proximal to the tooth, of the main body of the tube; and there is disposed a recess portion capable of receiving the extremity of an instrument for dental surgery such as a pincette, etc. at a required position on the frontal surface of the main body of the tube, in order to try to solve the problems described previously.

By using the orthodontic buccal tube thus constructed, since there are no tie wings in the upper part of the main body of the tube, it is unlikely that the tooth opposite thereto is brought into contact therewith.

Furthermore, when securing the buccal tube to the surface of teeth by adhesion using an adhesive, it is possible to firmly and easily hold the buccal tube, thrusting it to the surface of the tooth, by putting the extremity of an instrument for dental surgery such as a pincette 14, etc. in the recess portion 13 disposed on the frontal side of the main body of the tube to press it against the tooth.

DETAILED DESCRIPTION

Figure 1:
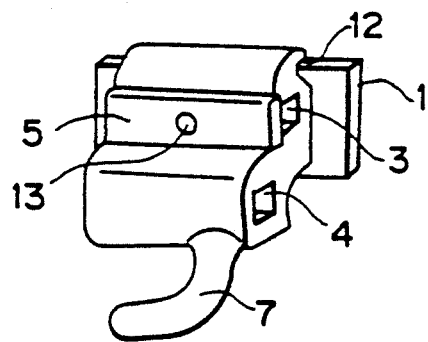
FIG. 1 is a perspective view of a buccal tube, which is an embodiment of the present invention.
Figure 2:
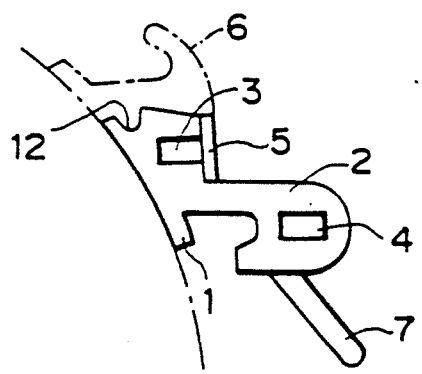
FIG. 2 is a side view thereof.
Figure 3:
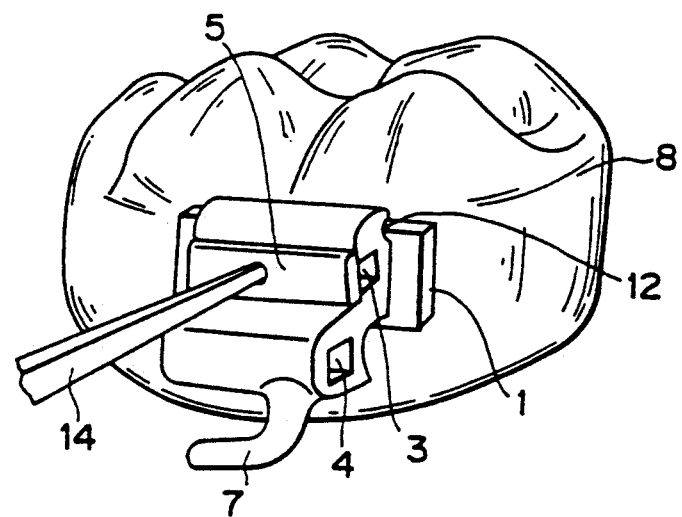
FIG. 3 is a perspective view showing a state, in which the buccal tube is adhered to the surface of a tooth.
Figure 4:
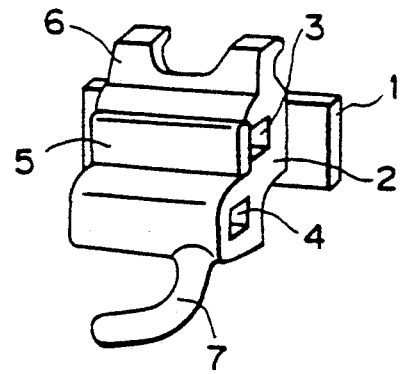
FIG. 4 is a perspective view of a prior art buccal tube.
Figure 5:
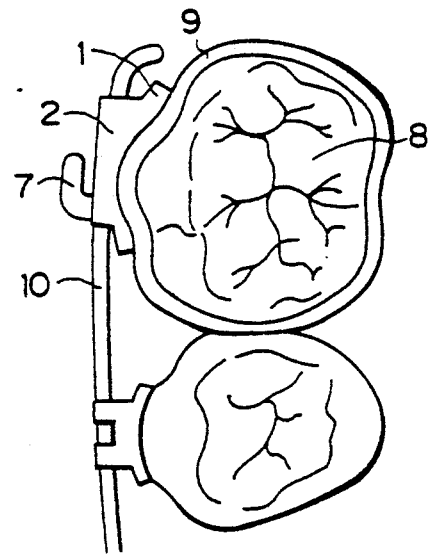
FIG. 5 is a plan view showing a state, in which the buccal tube indicated in FIG. 4 is mounted on a first molar tooth.
Figure 6:
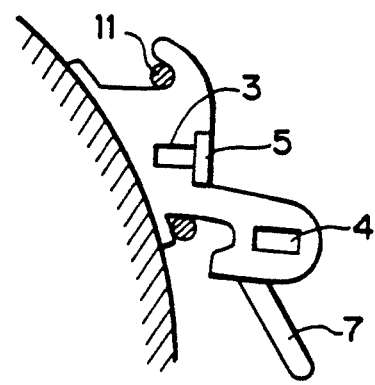
FIG. 6 is a side view showing a state, in which a ligature is mounted on the same buccal tube.

FIGS. 1 to 3 show an embodiment of the present invention. Members identical or similar to those described previously are indicated by the same reference numerals.

That is, reference numeral 1 is a base portion of the buccal tube; 2 is the main body of the tube; 3 is a throughhole serving as the main tube; 4 is a throughhole serving as the auxiliary tube; 5 is a cover cap for the throughhole 3; and 7 is a hook. The effective height of the main body of the tube is restricted to a certain value obtained by removing the portion corresponding to the tie wings of the prior art buccal tube, and there is formed a groove 12 for receiving a ligature in a part on the occlusal side, proximal to the tooth. On the other hand, a recess portion 13 is formed in the surface portion of the cover cap 5 on the frontal side of the main body 2 of the tube.

In the buccal tube having the construction described above, since there is no part corresponding to the prior art tie wings 6 on the main body 2 of the tube, the concern that the buccal tube may be brought into contact with the cusp of the opposite tooth thereto is alleviated. Furthermore, although the part corresponding to the tie wings 6 is removed, since there is the groove for receiving a ligature in the part on the occlusal side, proximal to the tooth, ligation using the ligature can be effected similarly to the prior art buccal tube.

In addition, when securing the buccal tube described above directly to the surface of the tooth by adhesion, the extremity of the dental pincette 14 is put in the recess portion 13 formed in the buccal tube to press it against the tooth, as indicated in FIG. 3. In this way, since the extremity of the pincette can be linked with the main body of the tube without slipping, it is possible to stably the buccal tube, until the adhesive is hardened.

The recess portion 13 is useful, particularly when it is present in a buccal tube for a second molar tooth. For example, when it is present in a tube having a half-pear-shaped cross-section, the tube can be pressed more surely and more easily against the surface of the tooth. This can be applied indifferently to the upper jaw and the lower jaw.

Furthermore, as described previously, particularly in the case where the present invention is applied to a buccal tube with torque, since the distance between the base of the throughhole 3 serving as the main tube and the base of the whole tube can be great for a constructional reason, it is possible to position the newly provided groove 12 for ligature more closely to the gingiva side.

Although in the above embodiment the recess portion 13 is disposed on the cover cap 5, this recess portion 13 may be positioned on another part, if it is such a position that a pressing force exerted by a pincette, etc. acts usefully.

As explained above, according to the present invention, since there is no part corresponding to the tie wings, it is possible to reduce the height of the buccal tube by about 30% with respect to that of the prior art buccal tube. Consequently, since it is possible to set the buccal tube at a more suitable position and owing to the shape it is not feared that the tie wings are brought into contact with the tooth opposite thereto, the risk that of artificial wear by occlusion is reduced.

Further, in the case where the present invention is applied to a buccal tube to be adhered to a tooth, adhering work for the buccal tube can be effected more easily.

What is claimed is:

1. An orthodontic buccal tube, comprising a main body having on one side thereof a first surface adapted for engagement with a tooth, having on an upper side thereof an upwardly facing second surface, having in said second surface a groove which extends approximately parallel to said first surface, having a throughhole extending therethrough below said second surface in a direction approximately parallel to said first surface, having on a side thereof opposite from said first surface a third surface facing in a direction approximately opposite said first surface, and having a recess which extends thereinto from said third surface and which is shaped to receive an end portion of a tool, wherein said main body includes a projection which projects approximately horizontally outwardly beyond said third surface from a location below said third surface, and includes an auxiliary hole which extends through said projection adjacent an outer end thereof in a direction approximately parallel to said first surface.

2. An orthodontic buccal tube according to claim 1, including a hook provided on an underside of said projection.

3. An orthodontic buccal tube according to claim 1, wherein said main body is free of tie wings projecting upwardly above said second surface.

4. An orthodontic buccal tube, comprising a main body having on one side thereof a first surface adapted for engagement with a tooth, having on an upper side thereof an upwardly facing second surface, having in said second surface a groove which extends approximately parallel to said first surface, having a throughhole extending therethrough below said second surface in a direction approximately parallel to said first surface, having on a side thereof opposite from said first surface a third surface facing in a direction approximately opposite said first surface, and having a recess which extends thereinto from said third surface and which is shaped to receive an end portion of a tool, wherein said recess is a shallow circular depression spaced inwardly from peripheral edges of said third surface, wherein said main body includes first and second parts, said first part having thereon said first surface and said second surface with said groove, and having on a side thereof opposite from said first surface a fourth surface which faces in a direction approximately opposite from said first surface, said fourth surface having therein a groove which extends approximately parallel to said first, second and fourth surfaces and which serves as said throughhole, said second part of said main body having thereon a fifth surface which is engageable with said fourth surface on said first part, said third surface being provided on a side of said second part opposite from said fifth surface and said second part having therein said recess, said main body further including means for releasably securing said first and second parts to each other.

* * * * *